(12) United States Patent
Alaoui-Jamali et al.

(10) Patent No.: US 6,395,312 B1
(45) Date of Patent: May 28, 2002

(54) ECHINOPS EXTRACT WITH ANTI-CANCER ACTIVITY

(75) Inventors: Moulay A. Alaoui-Jamali, Laval; Gerald Batist, Montreal; Lolita Zamir, Westmount, all of (CA)

(73) Assignee: McGill University, Montréal (CA)

( * ) Notice: Subject to any disclaimer, the term of this patent is extended or adjusted under 35 U.S.C. 154(b) by 0 days.

(21) Appl. No.: 09/530,866

(22) PCT Filed: Nov. 5, 1998

(86) PCT No.: PCT/CA98/01035

§ 371 (c)(1),
(2), (4) Date: Sep. 28, 2000

(87) PCT Pub. No.: WO99/24047

PCT Pub. Date: May 20, 1999

(30) Foreign Application Priority Data

Nov. 7, 1997 (CA) .............................................. 2220633

(51) Int. Cl.⁷ .............................................. A61K 35/78
(52) U.S. Cl. ....................... 424/764; 424/725; 424/773; 514/444
(58) Field of Search ....................... 514/444; 424/195.1, 424/725, 764, 773

(56) References Cited

U.S. PATENT DOCUMENTS 5,602,170 A    2/1997    Chang et al. ................ 514/444

OTHER PUBLICATIONS

Bost et al., 1954. Bulletin de l'Academie Veterinaire de France, 27:87–93.*
Zsolt et al., 1998. Acta Pharmaceutica Hungarica, 68:214–219.*
J. Bost et al.. 1954. Bul. Acad. Vet., 27:87–93.

* cited by examiner

*Primary Examiner*—Francisco Prats
*Assistant Examiner*—Kailash C. Srivastava
(74) *Attorney, Agent, or Firm*—Ogilvy Renault; France Côté

(57) ABSTRACT

The present invention relates to an Extract of *Echinops spinosus* L (Asteraceae) and organic solvent soluble fractions of the extract that may be used in the treatment of cancer.

1 Claim, 4 Drawing Sheets

ECHINOPS EXTRACT WITH ANTI-CANCER ACTIVITY

BACKGROUND OF THE INVENTION (a) Field of the Invention

The invention relates to an extract of *Echinops spinosus* L. (Asteraceae) and fractions thereof for use in the treatment of cancer; the invention also relates to the preparation of the extract and the fractions and pharmaceutical compositions containing them.

(b) Description of Prior Art

Cancers are uncontrolled cell proliferations that result from the accumulation of genetic changes in cells endowed with proliferative potential. After a variable latency period during which they are clinically silent, the malignant cells progress to aggressive invasive and metastatic stages with tumor formation, bleeding, susceptibility to infections, and wide-spread dissimination throughout the body.

Despite important advances in treatment, cancers still account for 28% of death in Western countries. Treatment of cancer has relied mainly on surgery, chemotherapy, radiotherapy and more recently immunotherapy. Significant improvement in outcome has occurred with the use of combined modalities, for a small number of cancers. However, for the most frequent types of cancers (lung, breast, colo-rectal and the leukemias) complete remission and cure has not been achieved. Therefore, the development of new approaches for treating cancer patients is critically needed particularly for those patients whose disease has progressed to a metastatic stage and are refractory to standard chemotherapy.

The leaves of *Echinops spinosus* L. (Asteraceae) have previously been used in local or herbal medicine to treat warts; and a peptide having vasoconstrictive properties has been isolated from the root of the plant.

It would be highly desirable to be provided with a novel therapy for cancer which overcome the drawbacks of the method of the prior art.

SUMMARY OF THE INVENTION

One aim of the present invention is to provide a dried extract of the roots of *Echinops spinosus* L. (Asteraceae) and fractions thereof that have been found to be useful in treating cancers.

In accordance with one aspect of the invention there is provided an anti-cancer pharmaceutical composition comprising an acceptable, effective anti-cancer amount of an extract of roots *Echinops spinosus* L. (Asteraceae) or an organic solvent soluble fraction thereof, in association with a pharmaceutically acceptable carrier.

In accordance with another aspect of the invention there is provided an extract of roots of *Echinops spinosus* L. (Asteraceae) or an organic solvent soluble fraction thereof, for use in the treatment of cancer.

In accordance with yet another aspect of the invention there is provided a method of treating cancer comprising administering to a patient, an acceptable, effective anti-cancer amount of an extract of roots of *Echinops spinosus* L. (Asteraceae) or an organic solvent soluble fraction thereof.

In accordance with still another aspect of the invention there is provided a method of producing an anti-cancer agent comprising organic solvent extraction of an extract of roots of *Echinops spinosus* L. (Asteraceae) to produce an organic solvent soluble extract, and chromatographic separation of fractions of said organic solvent soluble extract.

For the purpose of the present invention the following terms are defined below.

The term "anti-cancer therapy" is intended to mean growth inhibition/eradication of primary tumors, stabilization of tumor growth, inhibition of metastasis formation, or prevention of tumor formation. Furthermore, anticancer activity also covers any combination between our substances and other known or investigational anticancer agents, in order to improve the therapeutic efficacy of drugs.

DETAILED DESCRIPTION OF THE INVENTION

The organic solvent soluble fractions of the present invention are fractions soluble in organic solvents such as methanol, ethanol, ethyl acetate and dimethyl sulfoxide.

The invention is more especially concerned with the fractions which are soluble in the organic solvents but not soluble in water.

i) Extract of *Echinops spinosus* L. (Asteraceae)
ii) Fractions

The dried extract of *Echinops spinosus* L. (Asteraceae) is first treated with water to remove water soluble fractions of the extract, whereafter the residue is treated with an organic solvent, for example, ethyl acetate to dissolve the organic solvent soluble fractions.

The ethyl acetate soluble fractions are purified, for example, on charcoal and/or CELITE™ (trademark for diatomaceous earth) and individual fractions are separated by high-performance liquid chromatography.

The fractions recovered were dissolved in dimethyl sulfoxide or ethanol.

The samples when stored at −80° C. retained their activity even after four months.

The organic solvent soluble fractions and extract were found to have a strong antiproliferative activity in a panel of human cancer cell lines derived from breast, ovary, prostate and lung. In vivo, the fractions and extract demonstrate antimetastatic activity in animal models.

Figure 4:
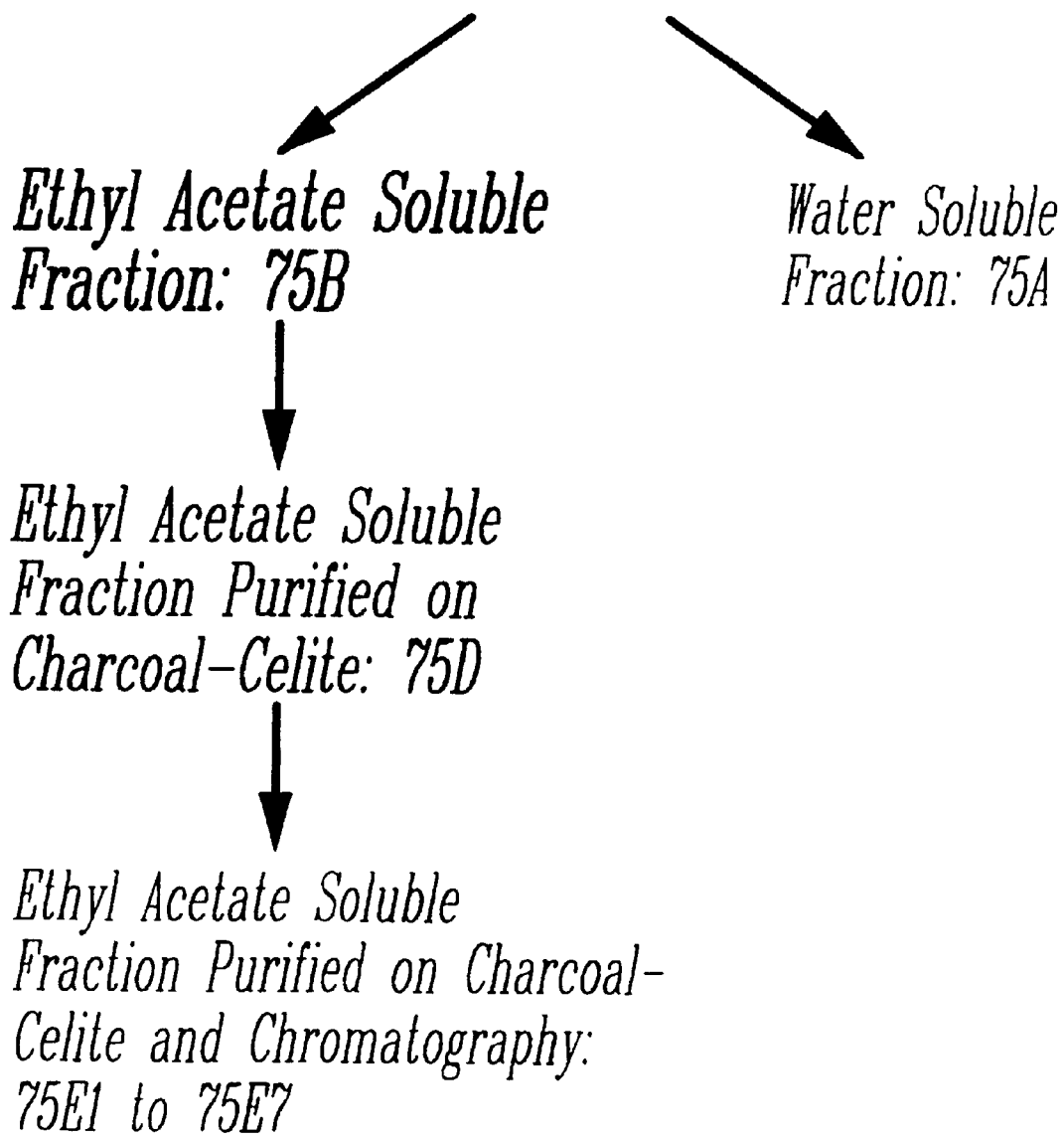
FIG. 4 illustrates a schematic representation of the process of fractionation.

The process of fractionation is illustrated schematically in FIG. 4.

The present invention will be more readily understood by referring to the following examples which are given to illustrate the invention rather than to limit its scope.

EXAMPLE I

In Vitro Antiproliferative Activity

Cell Lines and Cell Culture

Two cell lines were used to test for the antiproliferative activity of various fractions: human ovarian adenocarcinoma cell line A2780, and the human breast cancer cell line MCF7. Cells were grown in RPMI medium supplemented with 10% fetal bovine serum and penicillin-streptomycin antibiotics. Cells were maintained in culture at 37° C. in an atmosphere of 5% $CO_2$.

Cytotoxicity Assay

Exponentially growing cells ($2-3\times10^3$ cells/100 µl) were seeded in 96-well plates and incubated for 16 h. Cells were then treated continuously with the fractions. 72 h later, cell survival was evaluated by replacing the culture media with 150 µl fresh medium. containing 10 mM 4-(2-hydroxyethyl)-1-piperazine-ethanesulfonic acid buffer, pH 7.4 and 50 µl of 2.5 mg/ml of 3-(4,5-dimethylthiazo-2-yl)-2,5-diphenyl-tetrazolium bromide (MTT) in PBS, pH 7.4, were then added. After 3–4 h of incubation at 37° C., the medium and MTT were removed, and 200 µl of DMSO (dimethyl sulfoxide) was added to dissolve the precipitate of reduced MTT, followed by addition of 25 ml glycine buffer (0.1M glycine plus 0.1M NaCl, pH 10.5). The formazan crystals were then dissolved and the absorbance was determined at 570 nm with a microplate reader (BIORAD, model 450). The MTT assay distinguishes between viable and non-viable cells on the basis that physiologically active mitochondria metabolizes the MTT only in viable cells. The IC50 was calculated as the concentration of drug causing a 50% inhibition in the absorbance compared to cells treated with solvent alone.

Apoptosis Assay

Cells were seeded at $1\times10^6$ cells/T75 $cm^2$ plate, then left to attach overnight. The cells were then continuously exposed to the extracts for 72 hrs. Cells were then collected and washed 2x with PBS and then diluted to $1\times10^6$/100 µl PBS and placed in 96 well plate. Fixation was performed with 200 ml of 70% Ethanol with shaking at 4° C. for 30 min. Cells were then washed 1x with PBS, and permeabilized with 1% TRITON™ X-100 in 0.1% sodium citrate on ice for 2 min. Cells were washed 2x with PBS, and then labeled in 50 ml/well TUNEL reaction mixture of the Boehringer Mannheim In Situ cell death detection kit at 37° C. in the dark for 1 hr. Cells were then washed 3x with 1% BSA in PBS and resuspended in 500 µl PBS for analysis by flow cytometry. The cell death Tunnel assay estimates the extent of DNA fragmentation. The fragmented DNA is labeled at the free 3' OH group using terminal deoxynucleotide transferase. Fluoroscein labels are incorporated into nucleotide polymers that are attached to the DNA fragments. The labeling is specific to fragmented DNA and not degraded DNA due to the required presence of the 3' OH group. Thus, the level of fluorescence as measured by a flow cytometer is correlated to the level of DNA fragmentation, and hence to the number of apoptotic cells.

Results

Figure 1A:
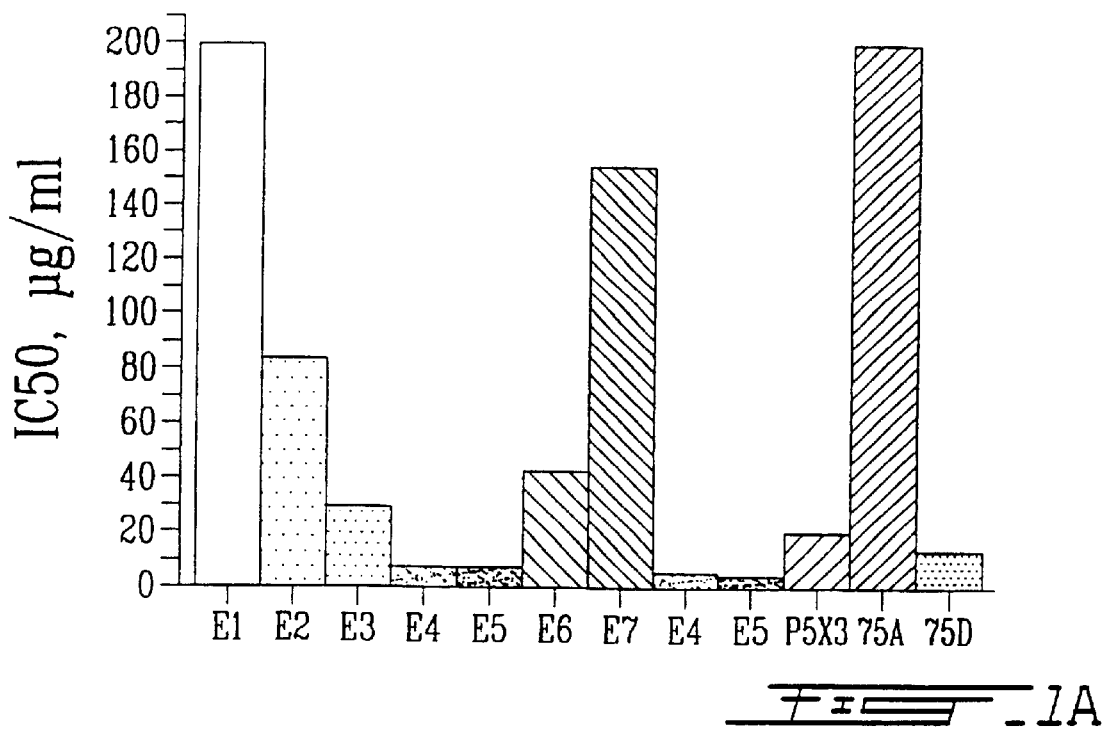
FIG. 1A illustrates the in vitro cytotoxicity of various fractions using human breast adenocarcinoma cell line, MCF7.
Figure 1B:
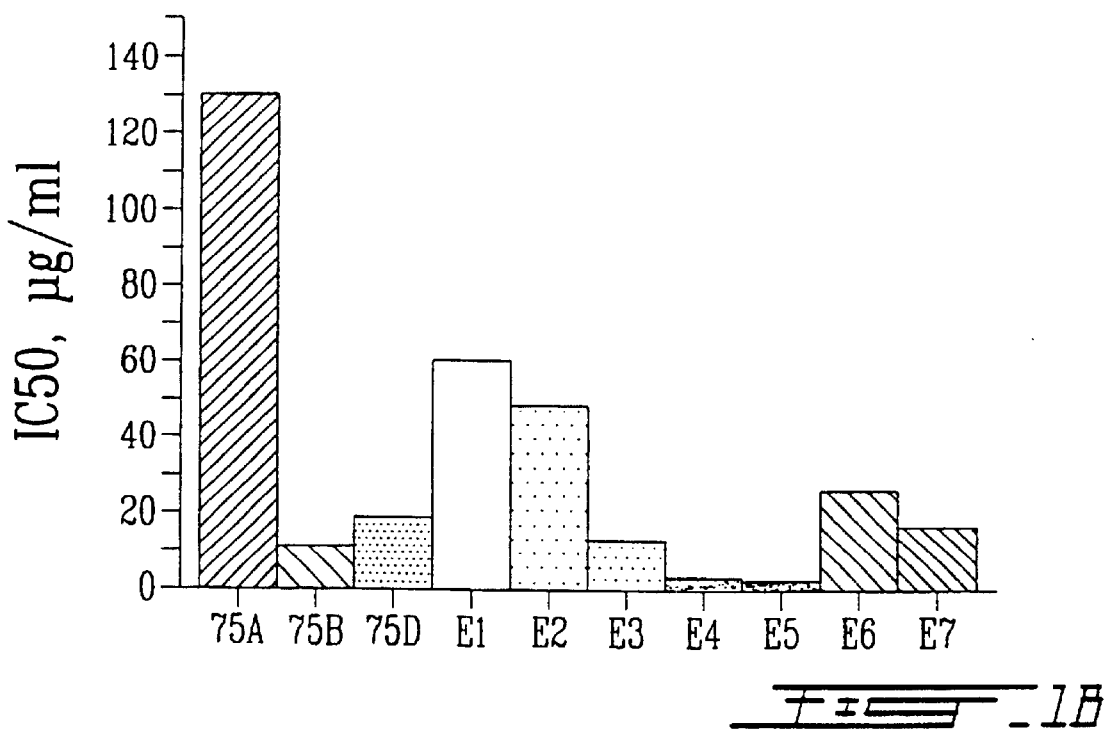
FIG. 1B illustrates the in vitro cytotoxicity of various fractions using human ovarian adenocarcinoma cell line, A2780.

Methanol soluble fractions, but not water soluble fractions, was found to have a potent antiproliferative activity in both A2780 and MCF7 cell lines. Further chromatographic fractionation of these organic soluble extract led to the isolation of 12 fractions referred to as E1–E12 (FIGS. 1A and 1B).

Morphological changes of cells treated with E fractions resembled those described with apoptosis-mediated cell death. Apoptosis was examined using ladder DNA and TUNEL Assays; it was found that some fractions, e.g. E4 and E5, induce apoptosis.

EXAMPLE II

In Vivo Study

Lewis Lung Carcinoma Cell Line and Cell Culture

The Lewis lung carcinoma clone, M47, with a high metastatic potential to the lung, was established and characterized (Brodt P., Cancer Res., 46: 2442, 1986). These cells were confirmed to be free of mycoplasma infection. Cells were maintained in RPMI-1640 medium supplemented with 10% fetal bovine serum and 1% penicillin-streptomycin, under 5% $CO_2$. Cells were passaged twice a week. Stocks of cells were generated and stored as early passages (passage no. 8–10 considering the initial stock received as passage no. 1). Cells were then propagated and stocks of the same passages were established and stored in liquid nitrogen for further studies with AETERNA compounds.

For tumor induction, cells were grown to 70% confluence in complete medium and then collected using trypsin-EDTA solution [0.05% trypsin, 0.53 mM EDTA-4Na in $H_BSS$ without Ca++, Mg++, and NaHCO3; Cellgro no. 25-052-Li]. Cells were then centrifuged and washed three times with phosphate buffer solution [D-PBS, Ca++ and Mg++ free; Cellgro no. 21-031-LV], and resuspended at a dilution of 0.1 to $1\times106$ cells/0.1 ml. Viability was examined by trypan blue staining and only flasks in which the viability was >95% were used for in vivo studies.

The mouse strain used in this study is C57BL/10 from the research laboratories. The animal room used has two doors, one serving as the entrance, and the other door provides direct access to washing/sterilization/incineration accurate adjustment of environmental parameters including temperature, humidity, ventilation, and lighting. Cleaning and sanitation practices are performed, on a daily basis, by personnel with appropriate training.

Tumor Cell Inoculation and Treatment

Animals were housed 5 per cage and were fed a diet of animal chow and water ad libitum. After one week acclimatization, LLC cells were transplanted subcutaneously, as a suspension of tumor cells [$2-5\times10^5$ viable cells per 0.1 ml], in the axillary region of the right flank. All animals were inoculated at the same site. Animals were subjected, on a daily basis, to general examination. Tumor growth was monitored every second or third day using calipers. Parameters measured are: tumor measured along the longest axis (length) and the perpendicular shortest axis (width) and the relative tumor volume (in $cm^3$) was calculated by the formula: [Length (cm) x(width $cm)^2$]/2. When the tumor reaches a size of 0.5–1.0 $cm^2$ (approximately 2–3 weeks), mice were randomized into three groups.

Animals were subjected to surgery to remove the primary tumor. The mice were lightly anesthetized with Forane. The skin overlying the tumor was cleaned with betadine and ethanol, in a laminar flow hood. A small skin incision (0.5–1 cm) was made using a sterile scalpel, and the tumor was carefully separated from the normal tissues (skin and muscle). LLC (at early stage of growth; 1–3 weeks) is well localized tumor and separation was easy to achieve without any significant damage to normal tissues. The tumor was removed, weighed and fixed for histopathology purposes. The wound was closed with surgical stainless steel clips (Autoclips; 9 mm; Clay Adams, Inc., Parsippany, N.J.). This site was further disinfected with betadine and the animal was housed as described above.

Mice were randomized after surgery into a group of 5 per cage. Cages were randomly assigned to specific experimental groups. The mice were then labeled by numbers using the "ear punching" method. Mice were checked on a daily basis to ensure the absence of infection. Animals with discomfort were sacrificed immediately. An additional extra-group of control mice was included to determine the optimal timing for sacrifice in order to obtain a significant number of well localized lung metastases. This group was subjected to the same experimental procedure as group 1 with the exception of drug treatment. Based on this group, a period of two weeks after removal of the primary tumor was sufficient to obtain an average of 20–30 nodules on the lung surface. Therefore, a two week period after primary tumor removal was used to sacrifice treated mice.

Dosing Schedule and Treatment

Figure 2:
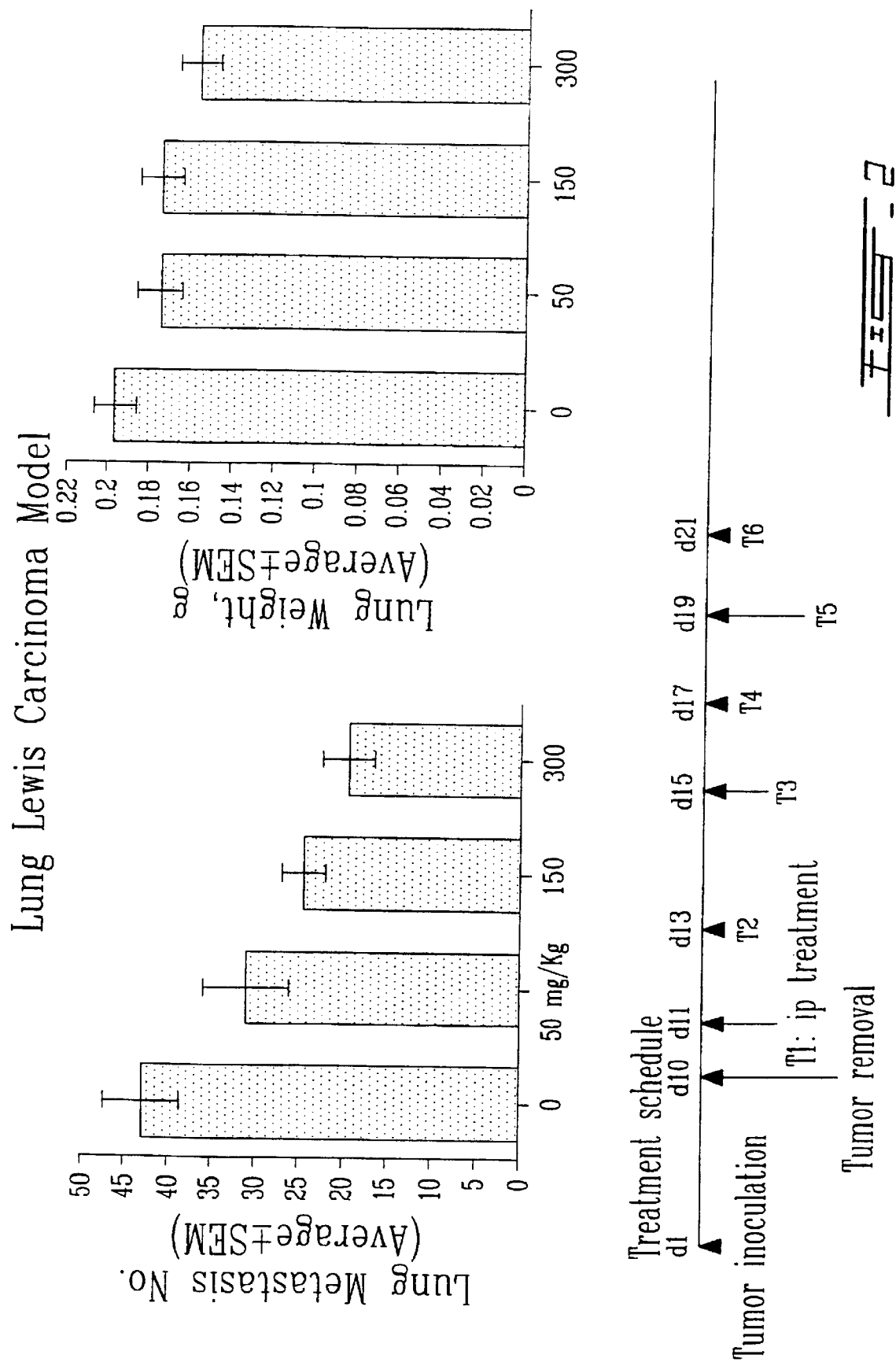
FIG. 2 illustrates the Lung Lewis carcinoma model schedule for drug treatment and also the antimetastatic activity of 75B.
Figure 3B:
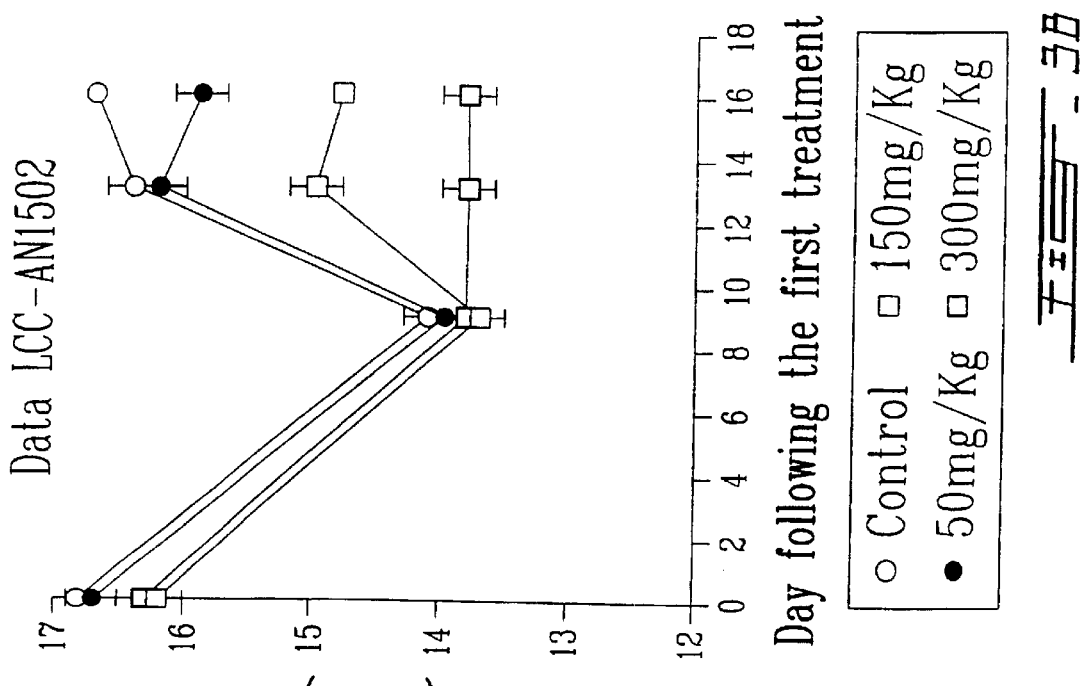
FIG 3A and 3B illustrate a schedule for drug treatment showing that doses used for the antimetastatic study have minor toxic effects to the host, since toxicity was observed only with very high doses >300.
Figure 3A:
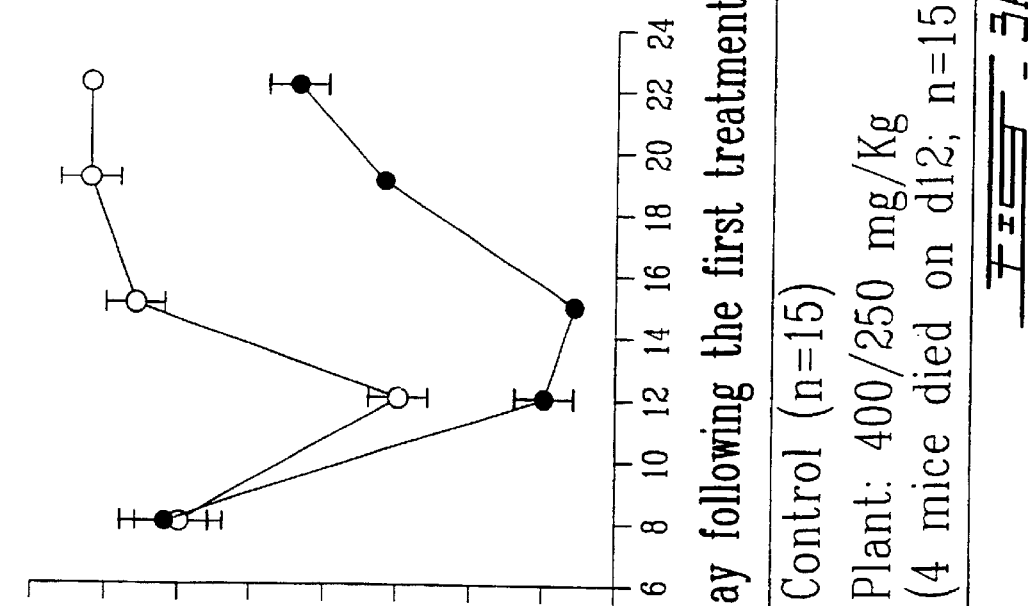

Drugs were given by gavage, using a 22 G curved feeding needle [total volume of 0.5 ml per animal], on a single daily basis administration after tumor cell inoculation. Control animals were given the same volume of saline solution [0.9% sodium chloride; Abbott Lab., lot no. 12 455 WS]. The dose of each drug was normalized to an average of 20 g body weight per animal. The schedules for drug treatment were based upon conditions described in FIGS. 2 and 3.

Animal Sacrifice, Tumor/organs Preparation

At the end of each experiment (a total of 5–8 weeks), animals were sacrificed in a $CO_2$ Chamber and autopsied. Tumors, organs or both were removed under sterile conditions [using a laminar flow hood]. Tumors were weighed. Organs (5 per group) were examined for gross pathological changes and then fixed in 10% formalin. Lungs were fixed in 10% Bouin's fixative diluted in a formalin solution, and lung surface metastases were counted using a stereomicroscope at 4× magnification or a magnifying-glass, and then lungs were embedded in paraffin wax according to standard procedures. Embedded tissues were stored for future histopathological studies.

Statistical Analysis

The umpaired Student t-test was used to compare statistical significance among various groups.

Results

Methanol soluble fraction was found to have a good antimetastatic activity in the Lewis lung carcinoma model. A dose relationship was also observed (see FIGS. 2 and 3).

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth, and as follows in the scope of the appended claims.

What is claimed is:

1. A method of treating cancer comprising administering to a patient a therapeutically effective anti-cancer amount of an extract of roots of *Echinops spinosus* L. (Asteraceae) or an organic solvent soluble fraction thereof, in association with a pharmaceutically acceptable carrier.

* * * * *